United States Patent
Rong et al.

(10) Patent No.: US 11,771,380 B2
(45) Date of Patent: Oct. 3, 2023

(54) VITAL SIGN MONITORING SYSTEM USING AN OPTICAL SENSOR

(71) Applicants: Yu Rong, Phoenix, AZ (US); Daniel W. Bliss, Scottsdale, AZ (US)

(72) Inventors: Yu Rong, Phoenix, AZ (US); Daniel W. Bliss, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 735 days.

(21) Appl. No.: 16/823,599

(22) Filed: Mar. 19, 2020

(65) Prior Publication Data

US 2020/0297227 A1    Sep. 24, 2020

Related U.S. Application Data

(60) Provisional application No. 62/820,569, filed on Mar. 19, 2019.

(51) Int. Cl.
*G06K 9/00* (2022.01)
*A61B 5/24* (2021.01)
(Continued)

(52) U.S. Cl.
CPC .......... *A61B 5/7282* (2013.01); *A61B 5/0075* (2013.01); *A61B 5/0816* (2013.01);
(Continued)

(58) Field of Classification Search
CPC ............ G06K 9/00; A61B 5/024; A61B 1/043
(Continued)

(56) References Cited

U.S. PATENT DOCUMENTS

| 8,483,761 B2 * | 7/2013 | Li ..................... H04B 7/0408 455/562.1 |
| 9,164,167 B2 | 10/2015 | Hyde et al. |

(Continued)

FOREIGN PATENT DOCUMENTS

| CN | 106264501 A | 1/2017 |
| EP | 3440991 A1 | 2/2019 |

(Continued)

OTHER PUBLICATIONS

Ali Al-Naji (Remote measurement of cardiopulmonary signal using an unmanned aerial vehicle IOP Publishing) (2018) (PDF).*

(Continued)

*Primary Examiner* — Seyed H Azarian
(74) *Attorney, Agent, or Firm* — Withrow & Terranova, P.L.L.C.; Vincent K. Gustafson

(57) ABSTRACT

A vital sign monitoring system using an optical sensor is provided. The vital sign monitoring system, and related methods and devices described herein, is equipped with a camera or other optical sensor to remotely detect and measure one or more physiological parameters (e.g., vital signs) of a subject. For example, the vital sign monitoring system can detect, measure, and/or monitor heart rates and respiration rates from one or multiple subjects simultaneously using advanced signal processing techniques, including adaptive color beamforming to more accurately detect and measure the vital sign(s) of interest.

18 Claims, 8 Drawing Sheets

(51) Int. Cl.
  *A61B 5/00* (2006.01)
  *A61B 5/08* (2006.01)
  *A61B 5/1171* (2016.01)
  *G06T 7/00* (2017.01)
  *A61B 5/024* (2006.01)
  *B64U 10/00* (2023.01)

(52) U.S. Cl.
  CPC ............ *A61B 5/1176* (2013.01); *A61B 5/444* (2013.01); *A61B 5/6887* (2013.01); *G06T 7/0012* (2013.01); *A61B 5/02427* (2013.01); *B64U 10/00* (2023.01)

(58) Field of Classification Search
  USPC ........ 382/100, 103, 106–108, 115–123, 128, 382/153, 162, 168, 181, 190, 199, 221, 382/254, 285–291, 305, 321; 600/476; 455/562.1; 705/2
  See application file for complete search history.

(56) References Cited

U.S. PATENT DOCUMENTS

| | | | |
|---|---|---|---|
| 9,737,219 | B2 | 8/2017 | Chen |
| 9,971,027 | B1 | 5/2018 | Stockmann et al. |
| 10,753,727 | B2 | 8/2020 | Klose et al. |
| 10,918,287 | B2 | 2/2021 | Islam |
| 10,928,374 | B2 | 2/2021 | Islam |
| 2008/0214903 | A1 | 9/2008 | Orbach |
| 2010/0152600 | A1 | 6/2010 | Droitcour et al. |
| 2012/0232388 | A1 | 9/2012 | Curra et al. |
| 2013/0030257 | A1 | 1/2013 | Nakata et al. |
| 2013/0300573 | A1 | 11/2013 | Brown et al. |
| 2013/0317377 | A1 | 11/2013 | Gupta et al. |
| 2014/0276089 | A1 | 9/2014 | Kirenko et al. |
| 2014/0276099 | A1 | 9/2014 | Kirenko et al. |
| 2014/0276104 | A1 | 9/2014 | Tao et al. |
| 2014/0378809 | A1 | 12/2014 | Weitnauer et al. |
| 2015/0342535 | A1* | 12/2015 | Chen ............... A61B 5/024 600/476 |
| 2015/0379370 | A1 | 12/2015 | Clifton et al. |
| 2016/0188831 | A1* | 6/2016 | Kurtz ............... G16H 10/60 705/2 |
| 2016/0287208 | A1 | 10/2016 | Zhai |
| 2016/0338604 | A1 | 11/2016 | Wang et al. |
| 2016/0343135 | A1 | 11/2016 | De Haan et al. |
| 2017/0042432 | A1 | 2/2017 | Adib et al. |
| 2017/0127988 | A1 | 5/2017 | Tao et al. |
| 2017/0174343 | A1 | 6/2017 | Erickson et al. |
| 2017/0341745 | A1* | 11/2017 | Sekine ............. G16H 40/67 |
| 2018/0049669 | A1 | 2/2018 | Vu et al. |
| 2018/0085009 | A1 | 3/2018 | Aiello et al. |
| 2018/0140255 | A1 | 5/2018 | Tao et al. |
| 2019/0050985 | A1 | 2/2019 | Den Brinker et al. |
| 2019/0057502 | A1 | 2/2019 | Wang et al. |
| 2019/0142289 | A1 | 5/2019 | Bliss et al. |
| 2019/0240535 | A1 | 8/2019 | Santra et al. |
| 2020/0271749 | A1* | 8/2020 | Wu ................. G01S 5/0278 |
| 2020/0302609 | A1 | 9/2020 | Rong et al. |
| 2022/0142478 | A1 | 5/2022 | Bliss et al. |

FOREIGN PATENT DOCUMENTS

| | | |
|---|---|---|
| EP | 3440996 A1 | 2/2019 |
| WO | 2009009690 A2 | 1/2009 |
| WO | 2013027027 A2 | 2/2013 |
| WO | 2016185004 A1 | 11/2016 |
| WO | 2017180985 A1 | 10/2017 |
| WO | 2017195196 A1 | 11/2017 |
| WO | 2019126476 A1 | 6/2019 |
| WO | 2020072297 A1 | 4/2020 |
| WO | 2020191142 A1 | 9/2020 |
| WO | 2021202677 A1 | 10/2021 |

OTHER PUBLICATIONS

Yu et al. ("Heart Rate Estimation From Facial Images Using Filter Bank" - ISCCSP 2014—pp. 69-72 (IDS).*
Jensen et al ("Camera-based Heart Rate Monitoring"—Kgs. Lyngby 2014, pp. 1-58). (IDS).*
Esteep, J. et al., "Recovering Pulse Rate During Motion Artifact with a Multi-Imager Array for Non-Contact Imaging Photoplethysmography," 2014 IEEE International Conference on Systems, Man, and Cybernetics, Oct. 5-8, 2014, San Diego, CA, USA, 8 pages.
Rahman, H. et al., "Real Time Heart Rate Monitoring from Facial RGB Color Video using Webcam," 9th Annual Workshop of the Swedish Artificial Intelligence Society (SAIS), May 2016, 9 pages.
Yu et al., "Heart Rate Estimation from Facial Images using Filter Bank," 2014 6th International Symposium on Communications, Control and Signal Processing (ISCCSP), May 21-23, 2014, Athens, Greece, IEEE, 4 pages.
Final Office Action for U.S. Appl. No. 16/823,587, dated May 25, 2022, 34 pages.
Tang, M.-C. et al., "Single Self-Injection-Locked Radar With Two Antennas for Monitoring Vital Signs With Large Body Movement Cancellation," IEEE Transactions on Microwave Theory and Techniques, vol. 65, Issue 12, Dec. 2017, first published Nov. 2017, IEEE, 10 pages.
Theofanopoulos, P.C. et al., "A Terahertz Microscopy Technique for Sweat Duct Detection," 2018 IEEE/MTT-S International Microwave Symposium—IMS, Jun. 10-15, 2018, Philadelphia, PA, USA, IEEE, 4 pages.
Tripathi, S. et al., "Morphology of human sweat ducts observed by optical coherencetomography and their frequency of resonance in the terahertz frequency region," Scientific Reports, vol. 5, Article No. 9071, Mar. 2015, 7 pages.
Verkruysse, W. et al., "Remote plethysmographic imaging using ambient light," Optics Express, vol. 16, No. 26, Dec. 2008, 16 pages.
Wang, F.-K. et al., "Detection of Concealed Individuals Based on Their Vital Signs by Using a See-Through-Wall Imaging System With a Self-Injection-Locked Radar," IEEE Transactions on Microwave Theory and Techniques, vol. 61, Issue 1, Jan. 2013, Dec. 2012, IEEE, 9 pages.
Wang, W. et al., "Unsupervised Subject Detection via Remote-PPG," IEEE Transactions on Biomedical Engineering, vol. 62, No. 11, Nov. 2015, first published Jun. 2015, IEEE, 9 pages.
Wang, Y. et al., "Induction of model trees for predicting continuous classes," Proceedings of the poster papers of the 9th European Conference on Machine Learning, Apr. 1997, 12 pages.
Zhang, Q. et al., "Heart Rate Extraction Based on Near-Infrared Camera: Towards Driver State Monitoring," IEEE Access, vol. 6, Jun. 2018, IEEE, 11 pages.
Zhu et al., "Doppler Radar Techniques for Vital Signs Detection Featuring Noise Cancellations," 2019 IEEE MTT-S Interational Microwave Biomedical Conference, May 2019, IEEE, 6 pages.
Invitation to Pay Additional Fees for International Patent Application No. PCT/US2019/053425, dated Nov. 27, 2019, 2 pages.
International Search Report and Written Opinion for International Patent Application No. PCT/US2019/053425, dated Jan. 30, 2020, 10 pages.
International Preliminary Report on Patentability for International Patent Application No. PCT/US2019/053425, dated Apr. 15, 2021, 7 pages.
International Search Report and Written Opinion for International Patent Application No. PCT/US2021/025106, dated Jul. 20, 2021, 10 pages.
Aoyagi, T. et al., "Pulse oximetry: Its invention, contribution to medicine, and future tasks," Anesthesia and Analgesia, vol. 94, Feb. 2002, 5 pages.
Benton, C. et al., "Terahertz Radar for Remote Measurement of Vital Signs," 2008 Joint Meeting of the APS Ohio-Region Section, the AAPT Southern Ohio Section, and the ACS Dayton-Section, Oct. 10-11, 2008, Dayton, Ohio, American Physical Society, Abstract only, 1 page.

(56) References Cited

OTHER PUBLICATIONS

Rong, Y. et al., "Respiration and Cardiac Activity Sensing Using 3-D Cameras," 2020 54th Asilomar Conference on Signals, Systems, and Computers, Nov. 1-4, 2020, Pacific Grove, CA, USA, IEEE, 5 pages.

Theofanopoulos, P.C. et al., "A Novel Fingerprint Scanning Method Using Terahertz Imaging," 2018 IEEE International Symposium on Antennas and Propagation & USNC/URSI National Radio Science Meeting, Jul. 8-13, 2018, Boston, MA, USA, IEEE, 2 pages.

Jensen, J. et al., "Camera-based Heart Rate Monitoring," B.Sc. Thesis, Bachelor of Science in Engineering, Department of Applied Mathematics and Computer Science, Technical University of Denmark, 2014, 72 pages.

Unakafov, A., "Pulse rate estimation usinG imaging photoplethysmography: generic framework and comparison of methods on a publicly available dataset," arXiv:1710.08369v1 [eess.IV], Oct. 17, 2017, 17 pages.

Non-Final Office Action for U.S. Appl. No. 16/823,587, dated Oct. 24, 2022, 26 pages.

Extended European Search Report for European Patent Application No. 20772680.3, dated Nov. 8, 2022, 8 pages.

Ahmad, A. et al., "Vital signs monitoring of multiple people using a FMCW millimeter-wave sensor," 2018 IEEE Radar Conference (RadarConf 18), Apr. 23-27, 2018, Oklahoma City, OK, USA, IEEE, 6 pages.

Alizadeh, M. et al., "Remote Monitoring of Human Vital Signs Using mm-Wave FMCW Radar," IEEE Access, vol. 7, Apr. 2019, IEEE, 12 pages.

Anderson, N. et al., "A 118-mW Pulse-Based Radar SoC in 55-nm CMOS for Non-Contact Human Vital Signs Detection," IEEE Journal of Solid-State Circuits, vol. 52, No. 12, Dec. 2017, IEEE, pp. 3421-3432.

Anderson, R. et al., "The Optics of Human Skin," Journal of Investigative Dermatology, vol. 77, Issue 1, Jul. 1981, Elsevier, pp. 13-19.

Allen, J., "Photoplethysmography and its application in clinical physiological measurement," Physiological Measurement, vol. 28, No. 3, Feb. 2007, IOP Publishing, 40 pages.

Biswas, D. et al., "Heart Rate Estimation From Wrist-Worn Photoplethysmography: A Review," IEEE Sensors Journal, vol. 19, Issue 16, Aug. 2019, IEEE, pp. 6560-6570.

Chen, K.-M. et al., "An X-Band Microwave Life-Detection System," IEEE Transactions on Biomedical Engineering, vol. BME-33, Issue 7, Jul. 1986, IEEE, 5 pages.

Chen, V.C. et al., "Micro-Doppler effect in radar: phenomenon, model, and simulation study," IEEE Transactions on Aerospace and Electronic Systems, vol. 42, Issue 1, Jan. 2006, IEEE, 20 pages.

Chen, K-M. et al., "Microwave life-detection systems for searching human subjects under earthquake rubble or behind barrier," IEEE Transactions on Biomedical Engineering, vol. 47, Issue 1, Jan. 2000, IEEE, pp. 105-114.

Chen, V. et al., "Time-Frequency Transforms for Radar Imaging and Signal Analysis," Artech House, 2002, 233 pages.

Churkin, S. et al., "Millimeter-wave radar for vital signs monitoring," 2015 IEEE International Conference on Microwaves, Communications, Antennas and Electronic Systems (COMCAS), Nov. 2-4, 2015, Tel Aviv, Israel, IEEE, 4 pages.

Damianou, D., "The wavelength dependence of the photoplethysmogram and its implication to pulse oximetry," Ph.D Thesis,University of Nottingham, 1995, 223 pages.

Davila, M. et al., "The PhysioCam: Cardiac Pulse, Continuously Monitored by a Color Video Camera," Journal of Medical Devices, vol. 10, Issue 2, Jun. 2016, published online May 2016, 2 pages.

Fallow, B.A. et al., "Influence of skin type and wavelength on light wave reflectance," Journal of Clinical Monitoring and Computing, vol. 27, No. 3, Feb. 2013, 7 pages.

Feldman, Y. et al., "The electromagnetic response of human skin in the millimetre and submillimetre wave range," Physics in Medicine and Biology, vol. 54(11), Jul. 2009, 25 pages.

Fitzpatrick, T., "The validity and practicality of sun-reactive skin types I through VI," Archives of Dermatology, vol. 124, No. 6, Jun. 1988, pp. 869-871.

Gu, C. et al., "A Hybrid Radar-Camera Sensing System With Phase Compensation for Random Body Movement Cancellation in Doppler Vital Sign Detection," IEEE Transactions on Microwave Theory and Techniques, vol. 61, Issue 12, Dec. 2013, first published Nov. 2013, IEEE, 12 pages.

Hayut, I. et al., "The Helical Structure of Sweat Ducts: Their Influence on the Electromagnetic Reflection Spectrum of the Skin," IEEE Transactions on Terahertz Science and Technology, vol. 3, Issue 2, Mar. 2013, first published Dec. 2012, IEEE, 10 pages.

Holmes, G. et al., "Generating Rule Sets from Model Trees," 12th Australian Joint Conference on Artificial Intelligence, Dec. 1999, 9 pages.

Humphreys, K. et al., "Noncontact simultaneous dual wavelength photoplethysmography: a further step toward noncontact pulse oximetry," Review of Scientific Instruments, vol. 78, Issue 4, Apr. 2007, AIP Publishing, 7 pages.

Immoreev, I. et al., "UWB Radar for Patient Monitoring," IEEE Aerospace and Electronic Systems Magazine, vol. 23, Issue 11, Nov. 2008, IEEE, 8 pages.

IT'IS Foundation, "Overview —Database of Tissue Properties," 2010-2022, accessed Aug. 31, 2014 from https://itis.swiss/virtual-population/tissue-properties/database/database-summary/, 2 page.

Kamal, A. et al., "Skin photoplethysmography—a review," Computer Methods and Programs in Biomedicine, vol. 28, No. 4, Apr. 1989, pp. 257-269.

Kamshilin, A. et al., A new look at the essence of the imaging photoplethysmography, Scientific Reports, vol. 5:10494, , May 2015, 9 pages.

Kebe, M. et al., "Human Vital Signs Detection Methods and Potential Using Radars: A Review," Sensors, vol. 20, Mar. 2020, MDPI, 38 pages.

Klemm, M. et al., "Breast Cancer Detection using Symmetrical Antenna Array," The Second European Conference on Antennas and Propagation, EuCAP 2007, Nov. 11-16, 2007, Edinburgh, IET, 5 pages.

Laman, N. et al., "High-Resolution Waveguide THz Spectroscopy of Biological Molecules," Biophysical Journal, vol. 94, Issue 3, Feb. 2008, pp. 1010-1020.

Lazaro, A. et al., "Analysis of Vital Signs Monitoring Using an IR-UWB Radar," Progress in Electromagnetics Research, vol. 100, Jan. 2010, pp. 265-284.

Li, C. et al., "Experiment and Spectral Analysis of a Low-Power Ka-Band Heartbeat Detector Measuring From Four Sides of a Human Body," IEEE Transactions on Microwave Theory and Techniques, vol. 54, Issue 12, Dec. 2006, IEEE, 9 pages.

Li, C. et al., "Random Body Movement Cancellation in Doppler Radar Vital Sign Detection," IEEE Transactions on Microwave Theory and Techniques, vol. 56, Issue 12, Dec. 2008, first published Nov. 18, 2008, IEEE, 4 pages.

Noon, D.A., "Stepped-Frequency Radar Design and Signal Processing Enhances Ground Penetrating Radar Performance," A thesis submitted for the degree of Doctor of Philosophy (PhD) of The University of Queensland, Jan. 1996, 186 pages.

Nowara, E. et al., "SparsePPG: Towards Driver Monitoring Using Camera-Based Vital Signs Estimation in Near-Infrared," 2018 IEEE/CVF Conference on Computer Vision and Pattern Recognition Workshops (CVPRW), Jun. 18-22, 2018, Salt Lake City, UT, USA, IEEE, 10 pages.

Orfanidis, S. J, "Electromagnetic Waves and Antennas," 2002, Rutgers University, 547 pages.

Petkie, D. et al., "Remote respiration and heart rate monitoring with millimeter-wave/terahertz radars," Proceedings of SPIE, vol. 7117, Oct. 2008, 6 pages.

Petkie, D. et al., "Millimeter-Wave Radar for Vital Signs Sensing," Radar Sensor Technology XIII Conference, Apr. 13-15, 2009, Orlando, FL, 5 pages.

Poh, M.-Z. et al., "Advancements in Noncontact, Multiparameter Physiological Measurements Using a Webcam," IEEE Transactions on Biomedical Engineering, vol. 58, Issue 1, Jan. 2011, Oct. 14, 2010, IEEE, 5 pages.

(56) References Cited

OTHER PUBLICATIONS

Quinlan, R., "Learning with Continuous Classes," 5th Australian Joint Conference on Artifical Intelligence, Nov. 1992, 6 pages.

Reid, C. et al., "Terahertz Time-Domain Spectroscopy of Human Blood," IEEE Journal of Biomedical and Health Informatics, vol. 17, Issue 4, Jul. 2013, first published Apr. 2013, IEEE, 11 pages.

Rong, Y. et al., "Active Breathing Suppression for Improved Sleep Monitoring Heartbeat Detection Using UWB Radar," 2019 IEEE 8th International Workshop on Computational Advances in Multi-Sensor Adaptive Processing (CAMSAP), Dec. 15-18, 2019, IEEE, 5 pages.

Rong, Y. et al., "Cardiac Sensing Exploiting an Ultra-Wideband Terahertz Sensing System," 2020 IEEE International Radar Conference (RADAR), Apr. 28-30, 2020, Washington, DC, USA, IEEE, 5 pages.

Rong, Y. et al., "Harmonics-Based Multiple Heartbeat Detection at Equal Distance using UWB Impulse Radar," 2018 IEEE Radar Conference (RadarConf18), Apr. 23-27, 2018, Oklahoma City, OK, USA, IEEE, 5 pages.

Rong, Y. et al., "Is Radar Cardiography (RCG) Possible?," 2019 IEEE Radar Conference (RadarConf), Apr. 22-26, 2019, Boston, MA, USA, IEEE, 6 pages.

Rong, Y. et al., "Multiple source detection performance of linear sparse arrays," 2016 50th Asilomar Conference on Signals, Systems and Computers, Nov. 6-9, 2016, Pacific Grove, CA, USA, IEEE, 5 pages.

Rong, Y. et al., "Non-Contact Vital Signs Detection with UAV-Borne Radars," arXiv:2011.13982v1 [eess.SP], Nov. 27, 2020, 7 pages.

Rong, Y. et al., "Smart Homes: See Multiple Heartbeats Through Wall Using Wireless Signals," 2019 IEEE Radar Conference (RadarConf), Apr. 22-26, 2019, Boston, MA, USA, IEEE, 6 pages.

Spetlik, R. et al., "Non-Contact Reflectance Photoplethysmography: Progress, Limitations, and Myths," 2018 13th IEEE International Conference on Automatic Face & Gesture Recognition (FG 2018), May 15-19, 2018, IEEE, 8 pages.

Staderini, E.M., "UWB Radars in Medicine," IEEE Aerospace and Electronic Systems Magazine, vol. 17, No. 1, Feb. 2002, pp. 13-18.

Sun, Y. et al., "Noncontact imaging photoplethysmography to effectively access pulse rate variability," Journal of Biomedical Optics, vol. 18, No. 6, Jun. 2013, 10 pages.

Tang, M.-C. et al., "A Self- and Mutually Injection-Locked Radar System for Monitoring Vital Signs in Real Time With Random Body Movement Cancellation," IEEE Transactions on Microwave Theory and Techniques, vol. 64, Issue 12, Dec. 2016, first published Nov. 2016, IEEE, 11 pages.

Final Office Action for U.S. Appl. No. 16/190,687, dated May 12, 2021, 5 pages.

Advisory Action for U.S. Appl. No. 16/190,687, dated Jul. 26, 2021, 3 pages.

Notice of Allowance for U.S. Appl. No. 16/190,687, dated Aug. 31, 2021, 9 pages.

Al-Naji, A. et al., "Remote Optical Cardiopulmonary Signal Extraction With Noise Artifact Removal, Multiple Subject Detection & Long-Distance," IEEE Access, vol. 6, 2018, IEEE, pp. 11573-11595.

Author Uknown, "Apple Watch Series 5," accessed Nov. 16, 2018 from https://www.apple.com/apple-watch-series-4/health/, 13 pages.

Author Uknown, "Shimmer3 ECG Unit," accessed Nov. 16, 2018 from http://www.shimmersensing.com/products/shimmer3-ecg-sensor, 6 pages.

Doerry, A., "Just Where Exactly is the Radar? (a.k.a. The Radar Antenna Phase Center)," Sandia Report SAND2013-10635, Dec. 2013, Sandia National Laboratories, 26 pages.

Fox, K. et al., "Resting Heart Rate in Cardiovascular Disease," Journal of the American College of Cardiology, vol. 50, No. 9, 2007, Elsevier Inc., pp. 823-830.

Guan, S. et al., "Automated DC Offset Calibration Strategy for Structural Health Monitoring Based on Portable CW Radar Sensor," IEEE Transactions on Instrumentation and Measurement, vol. 63, No. 12, Dec. 2014, IEEE, pp. 3111-3118.

Li, Changzhi, "Doppler Phase Modulation Effect for Non-contact Accurate Measurement of Vital Signs and other Periodic Movements—From Theory to CMOS System on Chip Integrations," A Dissertation presented to the Graduate School of the University of Florida, 2009, 129 pages.

Lin, J., "Noninvasive Microwave Measurement of Respiration," Proceedings of the IEEE, Oct. 1975, IEEE, p. 1530.

Ren, L. et al., "Phase-Based Methods for Heart Rate Detection Using UWB Impulse Doppler Radar," IEEE Transactions on Microwave Theory and Techniques, vol. 64, Issue 10, Oct. 2016, IEEE, 13 pages.

Rong, Y. et al., "Direct RF Signal Processing for Heart-Rate Monitoring Using UWB Impulse Radar," 2018 52nd Asilomar Conference on Signals, Systems, and Computers, Oct. 28-31, 2018, Pacific Grove, CA, IEEE, pp. 1215-1219.

Rong, Y. et al., "Remote Sensing for Vital Information Based on Spectral-Domain Harmonic Signatures," IEEE Transactions on Aerospace and Electronic Systems, vol. 55, No. 6, Dec. 2019, OAPA, pp. 3454-3465.

Singh, A. et al., "Data-Based Quadrature Imbalance Compensation for a CW Doppler Radar System," IEEE Transactions on Microwave Theory and Techniques, vol. 61, No. 4, Apr. 2013, IEEE, pp. 1718-1724.

Wang, S. et al., "A Novel Ultra-Wideband 80 GHz FMCW Radar System for Contactless Monitoring of Vital Signs," 2015 37th Annual International Conference of the IEEE Engineering in Medicine and Biology Society (EMBC), Aug. 25-29, 2015, Milan, Italy, IEEE, pp. 4978-4981.

Wolff, C., "Organ-Pipe Scanner," accessed Feb. 2019 from https://www.radartutorial.eu/06.antennas/an66.en.html, 1 page.

International Search Report and Written Opinion for International Patent Application No. PCT/US2020/023533, dated Jun. 18, 2020, 11 pages.

Fathy, Ramzie, et al., "Comparison of UWB Doppler radar and Camera based Photoplethysmography in Non-contact Multiple Heartbeats Detection," BioWireleSS, 2016, IEEE, pp. 25-28.

Feng, Litong, et al., "Motion-Resistant Remote Imaging Photoplethysmography Based on the Optical Properties of Skin," IEEE Transactions on Circuits and Systems for Video Technology, vol. 25, Issue 5, May 2015, pp. 879-891.

Gauri, Zade, "A Modem Microwave Life Detection System for Human Being Buried Under Rubble," International Journal of Advanced Engineering Research and Studies, vol. 1, Issue 1, Oct. 2011, 9 pages.

Hussain, Malek, "Ultra-Wideband Impulse Radar—An Overview of thePrinciples," IEEE AES Systems Magazine, vol. 13, Issue 9, Sep. 1998, pp. 9-14.

Lazaro, A., et al., "Analysis of Vital Signs Monitoring Using an IR-UWB Radar," Progress in Electromagnetics Research, vol. 100, 2010, pp. 265-284.

Li, Changzhi, et al., "Complex Signal Demodulation and Random Body Movement Cancellation Techniques for Non-contact Vital Sign Detection,"Microwave Symposium Digest, 2008, IEEE, pp. 567-570.

Park, Byung-Kown, et al., "Arctangent Demodulation With DC Offset Compensation in Quadrature Doppler Radar Receiver Systems," IEEE Transactions on Microwave Theory and Techniques, vol. 55, Issue 5, May 2007, pp. 1073-1079.

Poh, Ming-Zher, et al., "Non-contact, automated cardiac pulse measurements using video imaging and blind source separation," Optics Express, vol. 18, Issue 10, May 2010, 13 pages.

Ren, Lingyun, et al., "Noncontact Heartbeat Detection using UWB Impulse Doppler Radar," BioWireleSS, 2015, IEEE,pp 14-16.

Rong, Yu, et al., "Harmonics-Based Multiple Heartbeart Detection at Equal Distance using UWB Impulse Radar," IEEE Radar Conference, Apr. 2018, IEEE, pp. 1101-1105.

Singh, Megha, et al., "Reconstruction of Sequential Cardiac In-Plane Displacement Patterns on the Chest Wall by Laser Speckle Interferometry," IEEE Transactions on Biomedical Engineering, vol. 38, Issue 5, May 1991, pp. 483-489.

(56) References Cited

OTHER PUBLICATIONS

Wang, Jingyu, et al., "Noncontact Distance and Amplitude-Independent Vibration Measurement Based on an Extended DACM Algorithm," IEEE Transactions on Instrumentation and Measurement, vol. 63, Issue 1, Jan. 2014, pp. 145-153.

Yan, Jiaming, et al., "Through-Wall Multiple Targets Vital Signs Tracking Based on VMD Algorithm," Sensors, vol. 16, Issue 8, Aug. 2016, 11 pages.

Zade, G. et al., "A Modern Microwave Life Detection System for Human Being Buried Under Rubble", International Journal of Advanced Engineering Research and Studies, Oct. 2011, vol. 1, 9 pages.

Non-Final Office Action for U.S. Appl. No. 16/190,687, dated Jan. 12, 2021, 14 pages.

Nowara, E. et al., "PPGSecure: Biometric Presentation Attack Detection Using Photopietysmograms," 12th IEEE International Conference on Automatic Face & Gesture Recognition (FG 2017), May 30-Jun. 3, 2017, Washington, DC, USA, IEEE, 3 pages.

O'Brien, S., "Deepfakes are coming. Is Big Tech ready?" CNN Money, Aug. 8, 2018, 3 pages.

Wiede, C. et al., "Remote Heart Rate Determination in RGB Data," Proceedings of the 5th International Conference on Pattern Recognition Applications and Methods (ICPRAM 2016), Feb. 2016, Scitepress, pp. 240-246.

Youseph, S. et al., "Pixel and Edge Based Illuminant Color Estimation for Image Forgery Detection," Procedia Computer Science, vol. 46, Oct. 2015, Elsevier B.V., 8 pages.

Non-Final Office Action for U.S. Appl. No. 16/823,587, dated Nov. 23, 2021, 19 pages.

Notice of Allowance for U.S. Appl. No. 16/190,687, dated Dec. 24, 2021, 9 pages.

Final Office Action and Examiner-Initiated Interview Summary for U.S. Appl. No. 16/823,587, dated Mar. 2, 2023, 25 pages.

Advisory Action, Examiner-Initiated Interview Summary, and AFCP 2.0 Decision for U.S. Appl. No. 16/823,587, dated May 4, 2023, 5 pages.

Notice of Allowance for U.S. Appl. No. 16/823,587, dated May 26, 2023, 10 pages.

Non-Final Office Action for U.S. Appl. No. 17/277,596, dated Aug. 18, 2023, 10 pages.

\* cited by examiner

VITAL SIGN MONITORING SYSTEM USING AN OPTICAL SENSOR

RELATED APPLICATIONS

This application claims the benefit of provisional patent application Ser. No. 62/820,569, filed Mar. 19, 2019, the disclosure of which is hereby incorporated herein by reference in its entirety.

The present application is related to U.S. patent application Ser. No. 16/823,587, filed Mar. 19, 2020 (subsequently published as U.S. Patent Application Publication No. 2020/0302609 A1), entitled "DETECTING ABNORMALITIES IN VITAL SIGNS OF SUBJECTS OF VIDEOS," wherein each of the foregoing application and publication is hereby incorporated by reference herein in its entirety.

FIELD OF THE DISCLOSURE

This disclosure is related to optical vital sign detection.

BACKGROUND

Remote sensing of physiological parameters, such as heartbeat and breathing, has a number of uses. For example, this can facilitate prevention and early diagnosis of cardiovascular diseases. Conventional medical devices, such as electrocardiograms (ECGs), and more recent smart devices, such as smart wearable devices, can provide accurate heart rate measurement but require direct contact with the human body. These existing approaches can cause discomfort and may not be suitable for long-term monitoring of physiological parameters.

SUMMARY

A vital sign monitoring system using an optical sensor is provided. The vital sign monitoring system, and related methods and devices described herein, is equipped with a camera or other optical sensor to remotely detect and measure one or more physiological parameters (e.g., vital signs) of a subject. For example, the vital sign monitoring system can detect, measure, and/or monitor heart rates and respiration rates from one or multiple subjects simultaneously using advanced signal processing techniques, including adaptive color beamforming to more accurately detect and measure the vital sign(s) of interest.

Embodiments described herein use remote imaging photophlethysmography (RIPPG) to measure blood volume changes by detecting slight color variations in human skin using a non-contact video camera. Spatially averaged skin-pixel values are tracked and measured, such as by using a face tracking algorithm in individual video frames. By adaptively combining multi-color (e.g., red-green-blue (RGB)) time-series and concatenating resulting values, detected energy is maximized in a pulsatile direction to detect and measure the vital sign(s) of interest.

In some examples, the vital sign monitoring system is deployed in a movable device, such as a smart unmanned aerial vehicle (UAV or drone), which may be referred to herein as a BioDrone. The BioDrone is equipped with a camera or other optical sensor to remotely detect and measure one or more physiological parameters. The advanced signal processing techniques can compensate for drone flying motion and/or random body motion of one or more subjects to more accurately measure the desired physiological parameters.

An exemplary aspect relates to a method for remotely monitoring a physiological parameter. The method includes sensing optical video data of a subject, analyzing the optical video data to track color changes in a region of interest of the subject over time, and extracting physiological parameter data of the subject by adaptively beamforming the color changes.

Another exemplary aspect relates to a device. The device includes an optical image sensor and an image processor. The image processor is configured to receive optical video data from the optical image sensor, analyze the optical video data to track color changes in a region of interest of a subject over time, adaptively beamform the color changes, and analyze the beamformed color changes to determine a physiological parameter of the subject.

Another exemplary aspect relates to a vital sign monitoring system. The vital sign monitoring system includes a device comprising an optical image sensor and an image processor in communication with the optical image sensor. The image processor is configured to receive optical video data from the optical image sensor, analyze the optical video data to track color changes in a region of interest over time, and extract physiological parameter data of a human subject by adaptively beamforming the color changes.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

Figure 1A:
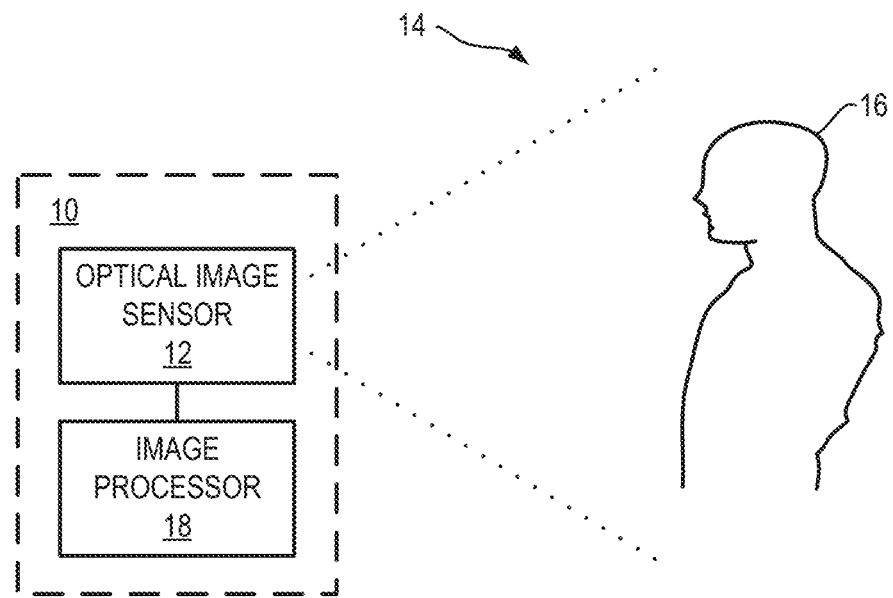
FIG. 1A is a schematic diagram of an exemplary vital sign monitoring system, which remotely detects one or more physiological parameters using an optical image sensor, such as a camera.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

A vital sign monitoring system using an optical sensor is provided. The vital sign monitoring system, and related methods and devices described herein, is equipped with a camera or other optical sensor to remotely detect and measure one or more physiological parameters (e.g., vital signs) of a subject. For example, the vital sign monitoring system can detect, measure, and/or monitor heart rates and respiration rates from one or multiple subjects simultaneously using advanced signal processing techniques, including adaptive color beamforming to more accurately detect and measure the vital sign(s) of interest.

Embodiments described herein use remote imaging photophlethysmography (RIPPG) to measure blood volume changes by detecting slight color variations in human skin using a non-contact video camera. Spatially averaged skin-pixel values are tracked and measured, such as by using a face tracking algorithm in individual video frames. By adaptively combining multi-color (e.g., red-green-blue (RGB)) time-series and concatenating resulting values, detected energy is maximized in a pulsatile direction to detect and measure the vital sign(s) of interest.

In some examples, the vital sign monitoring system is deployed in a movable device, such as a smart unmanned aerial vehicle (UAV or drone), which may be referred to herein as a BioDrone. The BioDrone is equipped with a camera or other optical sensor to remotely detect and measure one or more physiological parameters. The advanced signal processing techniques can compensate for drone flying motion and/or random body motion of one or more subjects to more accurately measure the desired physiological parameters.

FIG. 1A is a schematic diagram of an exemplary vital sign monitoring system 10, which remotely detects one or more physiological parameters using an optical image sensor 12, such as a camera. The optical image sensor 12 provides video data of a nearby environment 14 including one or more subjects 16 (e.g., human subject(s)). The vital sign monitoring system 10 includes an image processor 18 configured to extract vital signs of the subject(s) 16 from the video data provided by the optical image sensor 12.

The vital sign monitoring system 10 detects, measures, and/or monitors one or more physiological parameters of the subject(s) 16 with an RIPPG approach, using color beamforming and spectral analysis to extract the physiological parameter(s). RIPPG is an electro-optical technique for non-invasively measuring tissue blood volume pulses (BVPs) in the microvascular tissue bed underneath the skin. The approach described herein allows for a light source to be ambient light, but other light sources may be used as well.

Figure 1B:
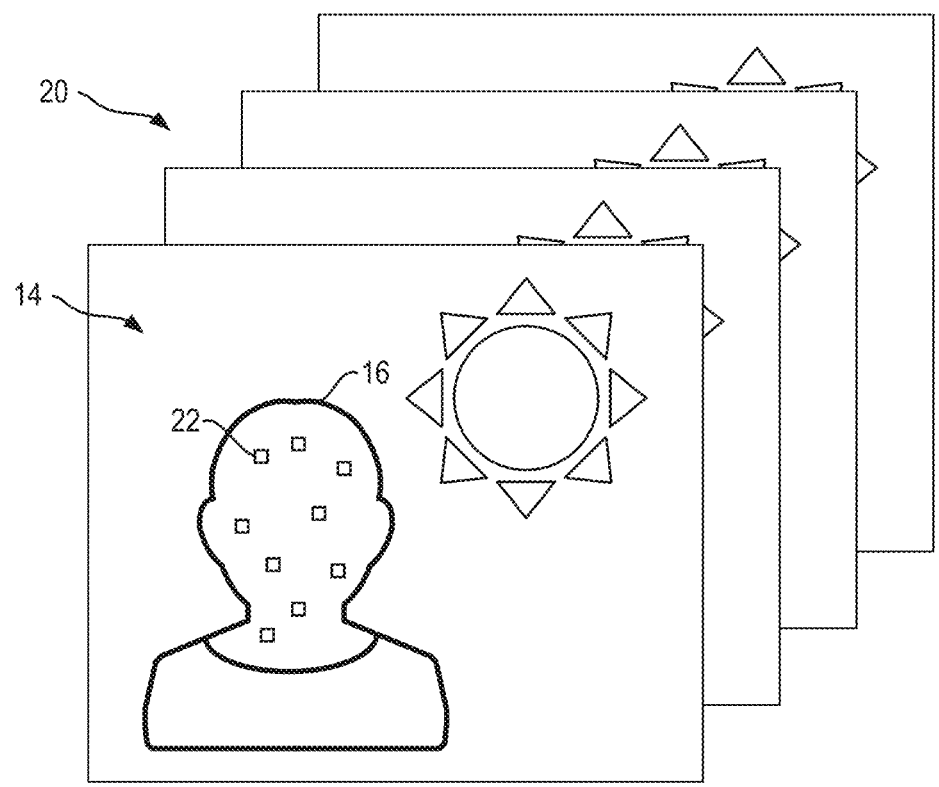
FIG. 1B is a graphical representation of an exemplary sequence of captured images of the environment of FIG. 1A.

FIG. 1B is a graphical representation of an exemplary sequence of captured images 20 of the environment 14 of FIG. 1A. The optical image sensor 12 (e.g., a digital camera) is focused on a region of interest 22 (represented as a set of sample pixels) on a human face of the subject 16. The sequence of captured images 20 can be recorded in a video format (e.g., a sequence of complete images or one or more reference images and difference vectors). The hemoglobin in blood can absorb light, therefore BVPs beneath the skin surface modulate light absorption by the skin during cardiac activity, appearing as slight color variations in the skin. These slight variations due to BVPs may be undetectable by human eyes, but the image processor 18 of the vital sign monitoring system 10 uses signal processing techniques to extract the BVPs and other vital signs (e.g., heart rate, heartbeat waveform, respiration rate).

Figure 2:
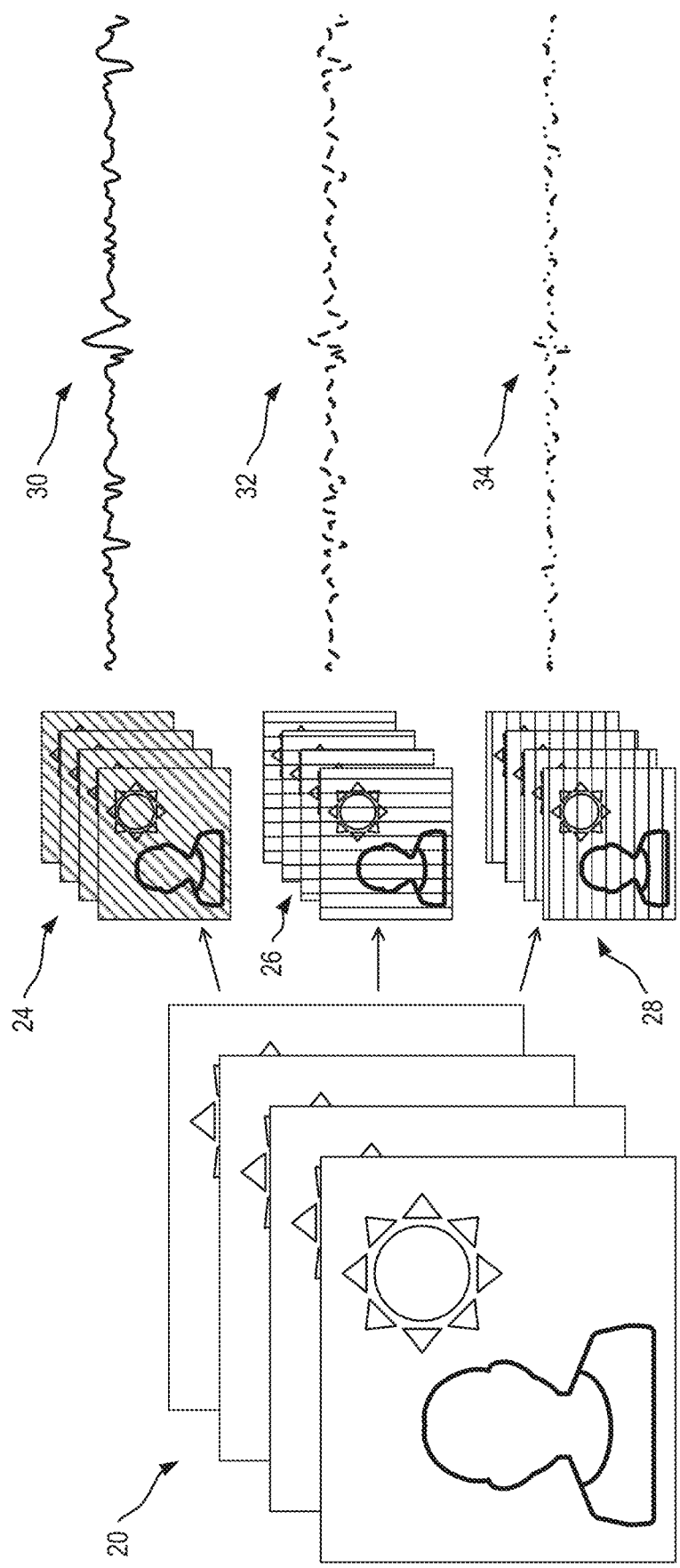
FIG. 2 is a schematic diagram of an exemplary approach to analyzing the sequence of captured images of FIG. 1B using color beamforming.

FIG. 2 is a schematic diagram of an exemplary approach to analyzing the sequence of captured images 20 of FIG. 1B using color beamforming. A spatially averaged red-green-blue (RGB) time-series can be obtained to describe skin color changes over time by averaging skin-pixel values selected from a face tracking algorithm in individual video frames and concatenating the resulting values from each color channel 24, 26, 28. For example, a red color channel 24 of the region of interest 22 can be spatially averaged and represented by a red time-series 30. Similarly, a green color channel 26 can be represented by a green time-series 32, and a blue color channel 28 can be represented by a blue time-series 34. Adaptive color beamforming is used to adaptively combine the RGB color time-series (combining the red time-series 30, the green time-series 32, and the blue time-series 34) and maximize the energy in the pulsatile direction.

Figure 3A:
FIG. 3A is a graphical representation of a traditional fixed color combining approach to photophlethysmography.

FIG. 3A is a graphical representation of a traditional fixed color combining approach to photophlethysmography. Under the traditional approach, only the red and green color channels are combined at a fixed ratio, such as by weighting the red time-series 30 of FIG. 2 at −0.71 and the green time-series 32 at 0.71 (while ignoring the blue time-series 34). This produces a red-green time-series 36.

Figure 3B:
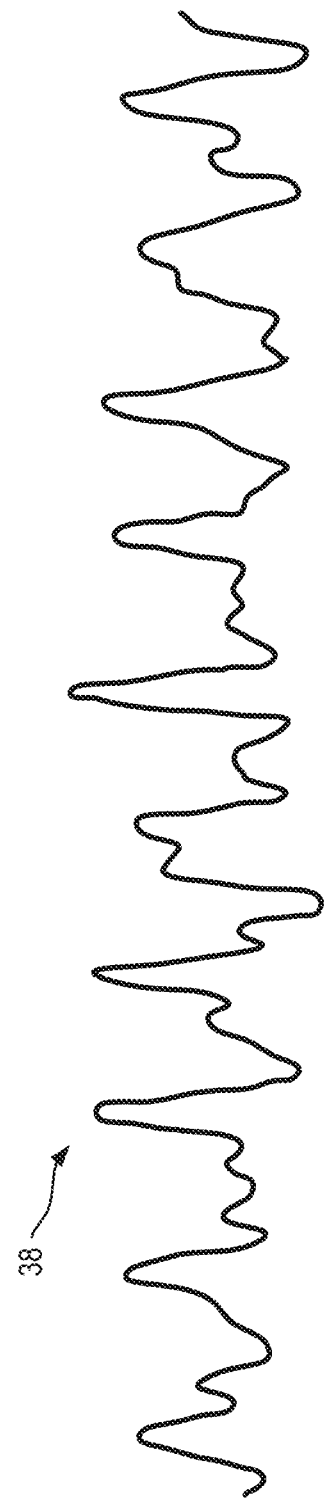
FIG. 3B is a graphical representation of results of the approach to analyzing the sequence of captured images of FIG. 2.

FIG. 3B is a graphical representation of results of the approach to analyzing the sequence of captured images of FIG. 2. Embodiments described herein apply adaptive color beamforming to adaptively combine the red time-series 30, the green time-series 32, and the blue time-series 34 of FIG. 2 into an RGB color time-series 38. The beamforming weights can be appropriately selected based on the spectral energy distribution of the RGB time-series 38 within the frequency range of a human heart rate. This exploits the facts that (1) the pulsatile motion in different color channels has the same frequency in the spectral domain, and (2) motions or changes in the background (e.g., illumination) varies across different spectral components.

An exemplary RGB color beamforming algorithm can be implemented as follows. The spatially averaged RGB color time-series are processed blockwise:

$$[R_j^i; G_j^i; B_j^i] = \left[ \frac{\sum_{ROI,k} pixel_k^{red}}{|ROI|}; \frac{\sum_{ROI,k} pixel_k^{green}}{|ROI|}; \frac{\sum_{ROI,k} pixel_k^{blue}}{|ROI|} \right]$$ Equation 1 where $R_j^i$ denotes the sample value at an i-th processing interval at a j-th index.

At every processing time, a total number of N samples is obtained, j=1, ..., N. |ROI| denotes the number of image pixels in the region of interest.

Two covariances are constructed based on the possible human heart rate frequency range. The spectral components within this region are used to construct a spectral covariance matrix that most likely contains the pulsatile information. The spectral components outside this region are treated as background noise and random motion not of interest, and thus can be used to build a noise-related covariance matrix. For a normal resting heart rate, the frequency is from about 50 to 100 beats per minute. The spatially averaged RGB color time-series are filtered at this frequency region:

$$[R_{hr}^i; G_{hr}^i; B_{hr}^i] = \text{filter}\{|R^i; G^i; B^i|\}$$ Equation 2 where $B^i$ is a 1 by N vector. The pulse related RGB covariance is given as:

$$COV_{hr}^i = \frac{1}{N}[R_{hr}^i; G_{hr}^i; B_{hr}^i][R_{hr}^i; G_{hr}^i; B_{hr}^i]^T$$ Equation 3 where T denotes matrix transpose.

For convenience, the entire RGB color time-series are used to construct the background covariance matrix since the heartbeat activity is limited in a small fraction of the entire spectrum. Similarly, the noise related covariance matrix is given as:

$$COV_{noi}^i = \frac{1}{N}[R^i; G^i; B^i][R^i; G^i; B^i]^T$$ Equation 4

In order to emphasize the pulsatile related spectral energy in the covariance matrix, a noise-suppressed pulsatile spectral covariance is obtained by multiplying the matrix inversion of the noise-related covariance matrix to the spectral covariance matrix:

$$COV_{sup}^i = \{COV_{noi}^i\}^{-1} COV_{hr}^i$$ Equation 5

Optimal beamforming weights are directly related to the direction represented by an eigenvector associated with the maximum eigenvalues of the noise-suppressed pulsatile spectral covariance matrix:

$$[\text{Vec}, \text{Val}] = \text{eig}\{COV_{sup}^i\}$$ Equation 6 where eig denotes the eigenvalue decomposition operation, and Vec and Val represent the eigenvector matrix and the associated eigenvalues. If both are sorted in descending order, the optimal color beamforming weight, a 3 by 1 vector, maximizing the pulse energy while suppressing the background noise is given as:

$$w_{hr}^{opt} \text{Vec}(:,1)$$ Equation 7

By applying the RGB color beamforming weights to the RGB color time-series, the desired pulsatile variation $p^i$ is obtained:

$$p^i = \{w_{hr}^{opt}\}^T [R^i; G^i; B^i]$$ Equation 8

This results in the RGB time-series 38, such as the example illustrated in FIG. 3B. Thus, the color beamforming approach outperforms the color difference algorithm of FIG. 3A.

Figure 4:
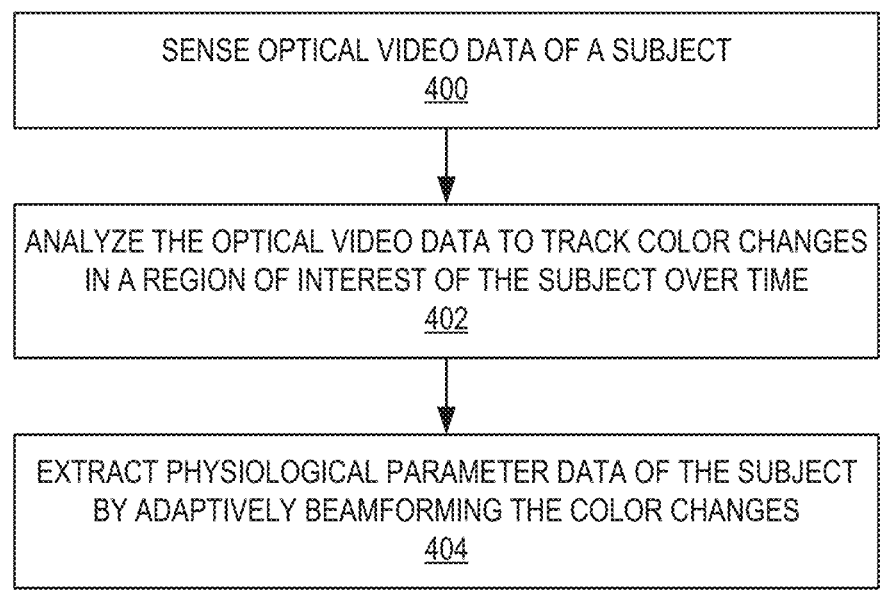
FIG. 4 is a schematic block diagram of an exemplary method for remotely monitoring a physiological parameter according to embodiments described herein.

FIG. 4 is a schematic block diagram of an exemplary method for remotely monitoring a physiological parameter according to embodiments described herein. The method begins with sensing optical video data of a subject (block 400). The method further includes analyzing the optical video data to track color changes in a region of interest of the subject over time (block 402). The method further includes extracting physiological parameter data of the subject by adaptively beamforming the color changes (block 404).

Figure 5:
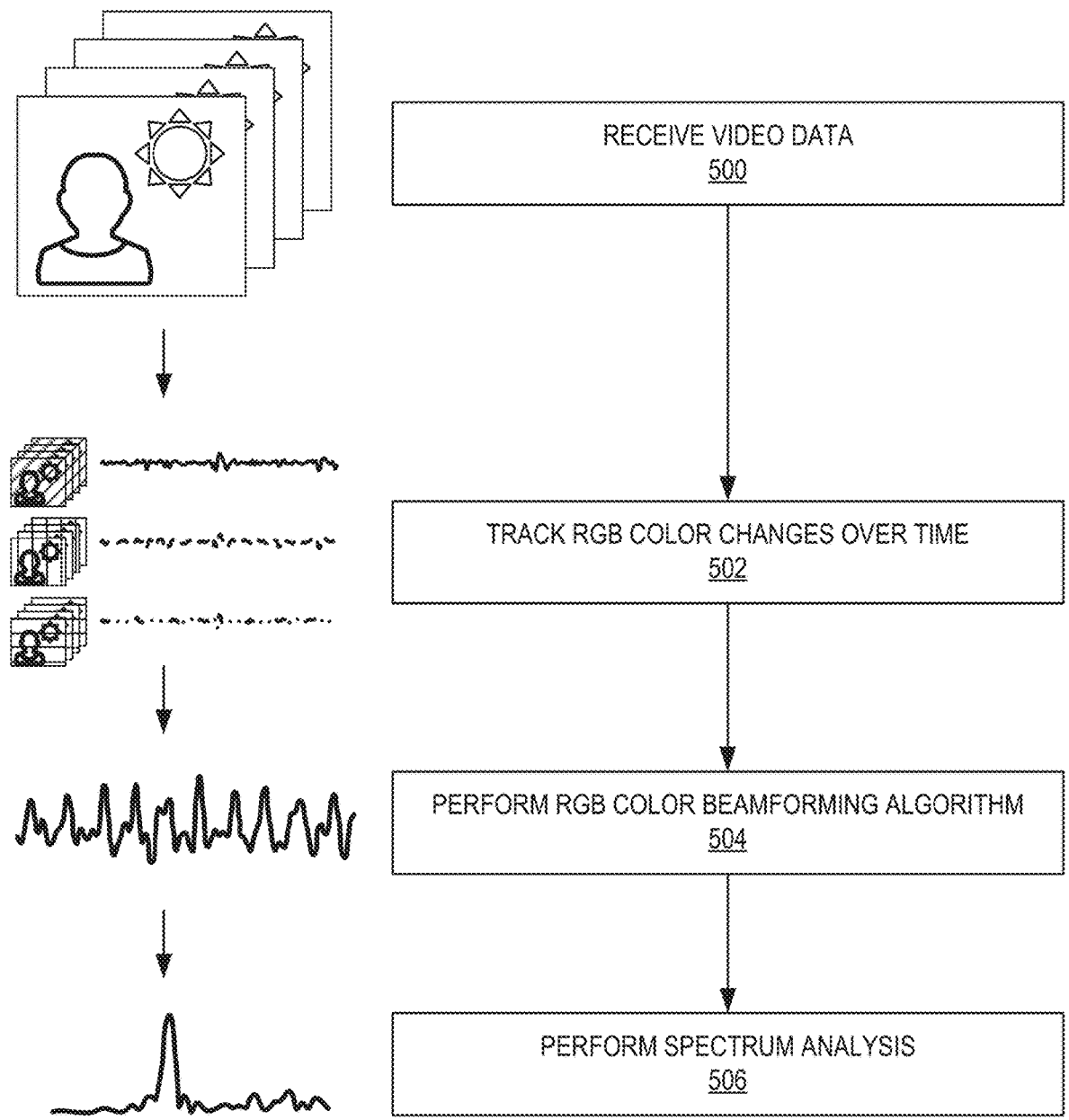
FIG. 5 is a schematic diagram of an exemplary remote imaging photophlethysmography (RIPPG) approach described herein using color beamforming and spectral analysis to extract vital signs of a subject.

FIG. 5 is a schematic diagram of an exemplary RIPPG approach described herein using color beamforming and spectral analysis to extract vital signs of a subject. With reference to FIGS. 2, 3B, and 5, the RIPPG approach can begin with receiving video data from the optical image sensor 12 focused on the region of interest 22 on the human face of the subject 16 (block 500). Changes in the sequence of captured images 20 are recorded and tracked over time (e.g., using the face tracking algorithm) and spatially averaged to produce the red time-series 30, the green time-series 32, and the blue time-series 34 (block 502).

The RGB beamforming algorithm described above is used to adaptively combine the red time-series 30, the green time-series 32, and the blue time-series 34 into the RGB color time-series 38 (block 504). The beamforming weights can be appropriately selected based on the spectral energy distribution of the RGB time-series 38 within the frequency range of a human heart rate (block 506). In this regard, the spectral components within the region of interest are used to construct the spectral covariance matrix that most likely contains the pulsatile information, where spectral components outside this region are treated as background noise to build a noise-related covariance matrix to further improve the extracted heart rate and/or heartbeat waveform.

The same concept described with regard to FIGS. 1A-5 above can be applied for respiration monitoring. There are two differences here: 1) the region of interest in the recorded images are different and 2) the spectral frequency range of interest is different. In order to obtain maximum respiration sensitivity, the region of interest is selected as a relevant body part, such as a subject's neck and/or front chest. In order to construct the respiratory related covariance matrix, the spatially averaged RGB color time-series at the respiration region of interest are filtered at a frequency region ranging from 10 to 30 breaths per minute. Then the remaining steps follow the approach described above.

Figure 6A:
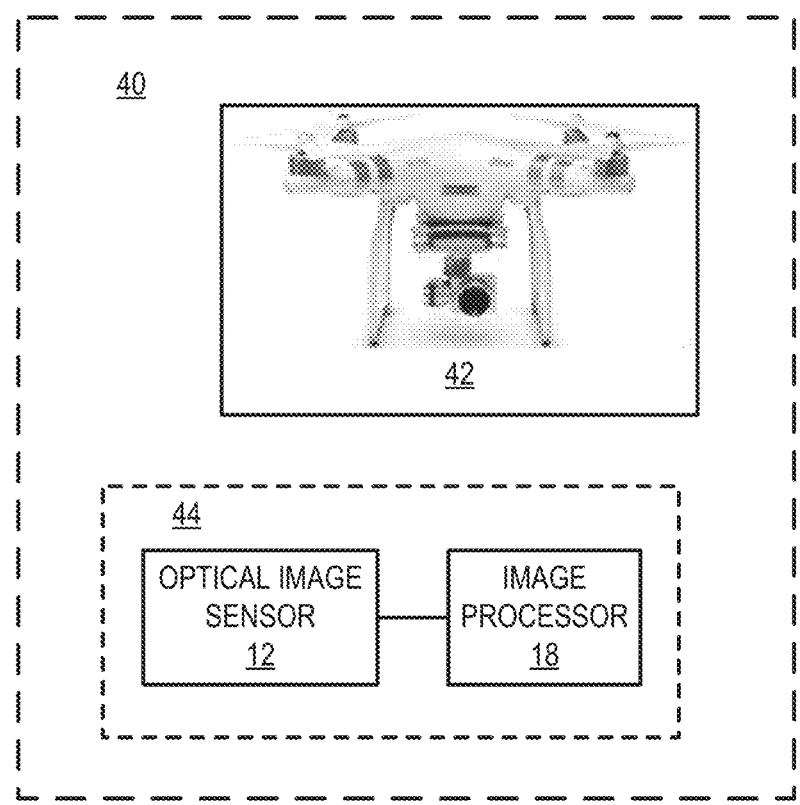
FIG. 6A is a schematic diagram of an exemplary BioDrone system.

FIG. 6A is a schematic diagram of an exemplary Bio-Drone system 40. The BioDrone system 40 includes a UAV 42 (e.g., a DJI phantom drone) as the flying platform. The UAV 42 is deployed with an optical image sensor 12 and an image processor 18 (e.g., a stand-alone mini control PC), as well as a portable battery. This forms a sensing module 44 which is used as a payload of the flying platform.

Figure 6B:
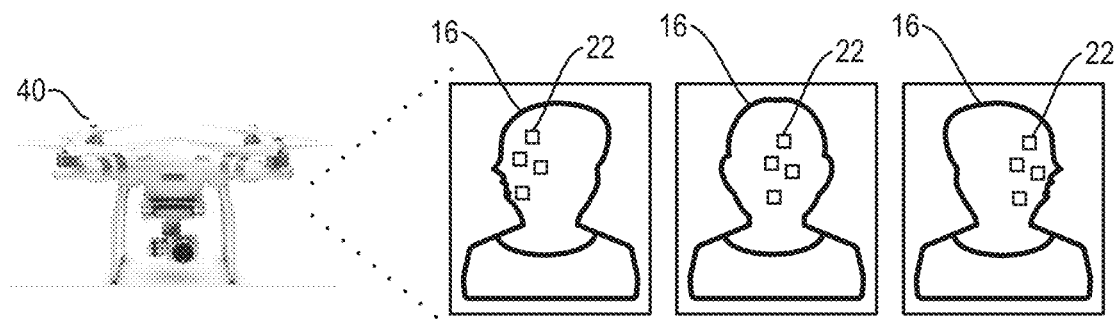
FIG. 6B is a schematic diagram of remote vital sign monitoring using the BioDrone system of FIG. 6A.

FIG. 6B is a schematic diagram of remote vital sign monitoring using the BioDrone system 40 of FIG. 6A. The BioDrone system 40 performs the vital sign monitoring approach described above with respect to FIGS. 1A-5, including by tracking motion of the region of interest 22 as the subject 16 moves and/or the BioDrone system 40 moves.

Figure 7:
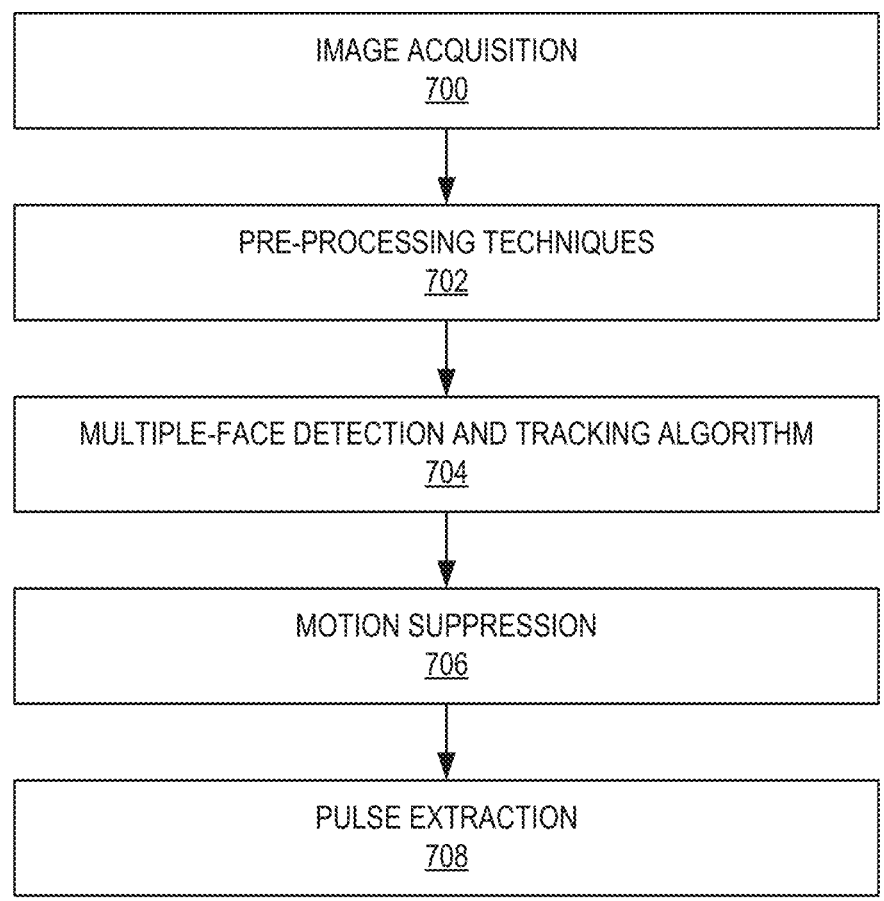
FIG. 7 is a process flow diagram for the BioDrone system of FIG. 6A.

FIG. 7 is a process flow diagram for the BioDrone system 40 of FIG. 6A, which can also be applied with respect to FIGS. 1A-5 above. The method can apply advanced imaging techniques to monitor physiological parameters, such as heart rate and respiration rate, from multiple subjects in optical video data received through an optical image sensor (e.g., camera). In order to detect the weak micro-motion of interest, some examples further address the following challenges: flying platform motion, random motion from the human subject, changes of possible illumination and pulse waveform reconstruction.

In order to address these issues, the remote vital sign system is designed accordingly. The image processor 18 applies a series of processing approaches:

Image acquisition (block 700)
Pre-processing techniques (block 702)
Multiple-face detection and tracking algorithm (block 704)
Motion suppression (block 706)
Pulse extraction algorithm (block 708)

The multiple-face detection and tracking algorithm (block 704) can effectively address the large-scale motions from the platform and body motion (e.g., head motion) of subjects. At the pre-processing stage (block 702), a signal magnification technique is applied to magnify the weak vital sign signal of interest. In order to further suppress any motion residuals (e.g., from small-scale motions), the RGB color beamforming algorithm described above with respect to FIGS. 1A-5 is applied to maximize the energy in the pulsatile direction (blocks 706 and 708).

Figure 8:
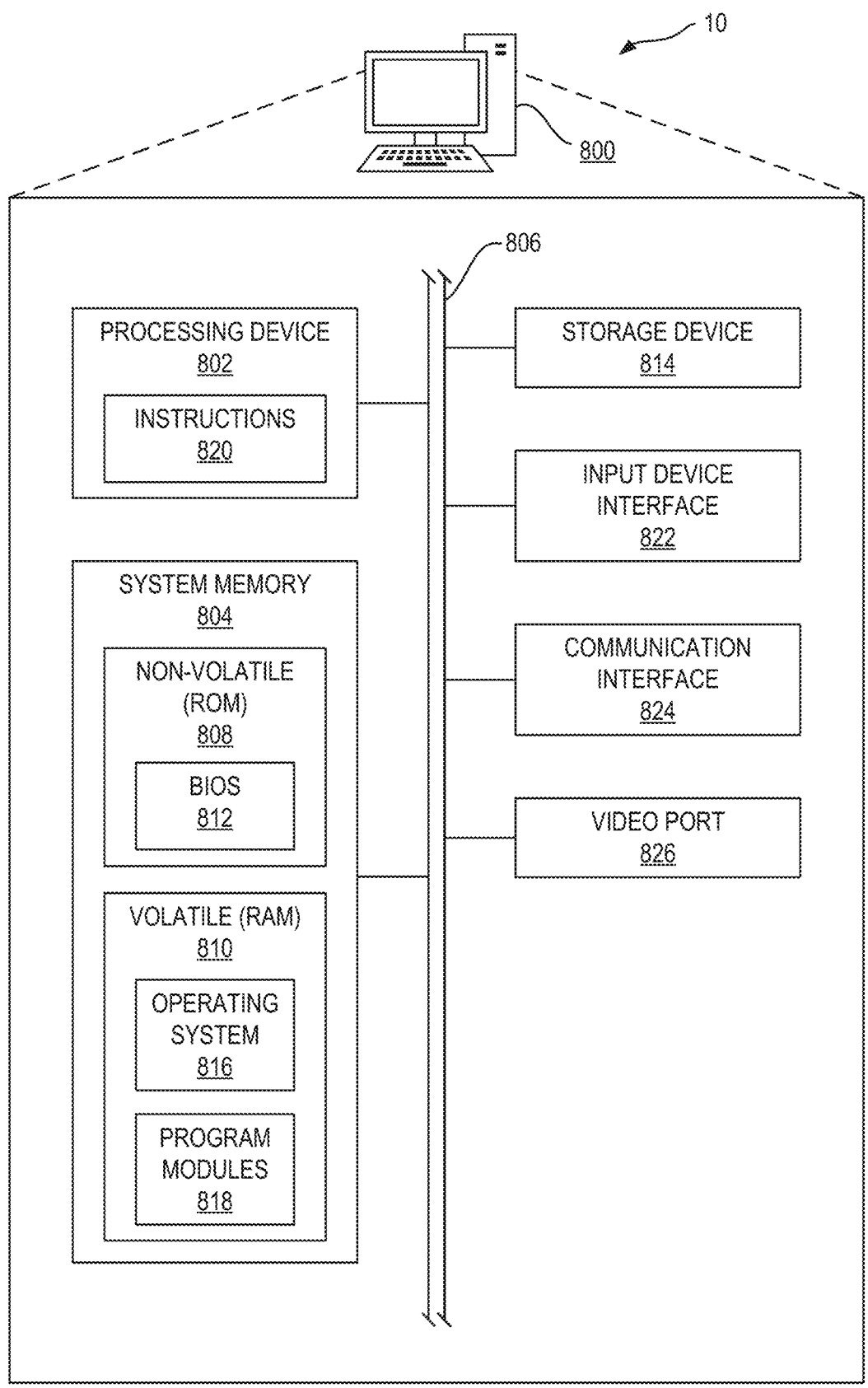
FIG. 8 is a block diagram of the vital sign monitoring system suitable for implementing remote monitoring of one or more physiological parameters according to embodiments disclosed herein.

FIG. 8 is a block diagram of the vital sign monitoring system 10 suitable for implementing remote monitoring of one or more physiological parameters according to embodiments disclosed herein. The vital sign monitoring system 10 includes or is implemented as a computer system 800, which comprises any computing or electronic device capable of including firmware, hardware, and/or executing software instructions that could be used to perform any of the methods or functions described above. In this regard, the computer system 800 may be a circuit or circuits included in an electronic board card, such as a printed circuit board (PCB), a server, a personal computer, a desktop computer, a laptop computer, an array of computers, a personal digital assistant (PDA), a computing pad, a mobile device, or any other device, and may represent, for example, a server or a user's computer.

The exemplary computer system 800 in this embodiment includes a processing device 802 or processor, a system memory 804, and a system bus 806. The system memory 804 may include non-volatile memory 808 and volatile memory 810. The non-volatile memory 808 may include read-only memory (ROM), erasable programmable read-only memory (EPROM), electrically erasable programmable read-only memory (EEPROM), and the like. The volatile memory 810 generally includes random-access memory (RAM) (e.g., dynamic random-access memory (DRAM), such as synchronous DRAM (SDRAM)). A basic input/output system (BIOS) 812 may be stored in the non-volatile memory 808 and can include the basic routines that help to transfer information between elements within the computer system 800.

The system bus 806 provides an interface for system components including, but not limited to, the system memory 804 and the processing device 802. The system bus 806 may be any of several types of bus structures that may further interconnect to a memory bus (with or without a memory controller), a peripheral bus, and/or a local bus using any of a variety of commercially available bus architectures.

The processing device 802 represents one or more commercially available or proprietary general-purpose processing devices, such as a microprocessor, central processing unit (CPU), or the like. More particularly, the processing device 802 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 802 is configured to execute processing logic instructions for performing the operations and steps discussed herein.

In this regard, the various illustrative logical blocks, modules, and circuits described in connection with the embodiments disclosed herein may be implemented or performed with the processing device 802, which may be a microprocessor, field programmable gate array (FPGA), a digital signal processor (DSP), an application-specific integrated circuit (ASIC), or other programmable logic device, a discrete gate or transistor logic, discrete hardware components, or any combination thereof designed to perform the functions described herein. Furthermore, the processing device 802 may be a microprocessor, or may be any conventional processor, controller, microcontroller, or state machine. The processing device 802 may also be implemented as a combination of computing devices (e.g., a combination of a DSP and a microprocessor, a plurality of microprocessors, one or more microprocessors in conjunction with a DSP core, or any other such configuration).

The computer system 800 may further include or be coupled to a non-transitory computer-readable storage medium, such as a storage device 814, which may represent an internal or external hard disk drive (HDD), flash memory, or the like. The storage device 814 and other drives associated with computer-readable media and computer-usable media may provide non-volatile storage of data, data structures, computer-executable instructions, and the like. Although the description of computer-readable media above refers to an HDD, it should be appreciated that other types of media that are readable by a computer, such as optical disks, magnetic cassettes, flash memory cards, cartridges, and the like, may also be used in the operating environment, and, further, that any such media may contain computer-executable instructions for performing novel methods of the disclosed embodiments.

An operating system 816 and any number of program modules 818 or other applications can be stored in the volatile memory 810, wherein the program modules 818 represent a wide array of computer-executable instructions corresponding to programs, applications, functions, and the like that may implement the functionality described herein in whole or in part, such as through instructions 820 on the processing device 802. The program modules 818 may also reside on the storage mechanism provided by the storage device 814. As such, all or a portion of the functionality described herein may be implemented as a computer program product stored on a transitory or non-transitory computer-usable or computer-readable storage medium, such as the storage device 814, non-volatile memory 808, volatile memory 810, instructions 820, and the like. The computer program product includes complex programming instructions, such as complex computer-readable program code, to cause the processing device 802 to carry out the steps necessary to implement the functions described herein.

An operator, such as the user, may also be able to enter one or more configuration commands to the computer system 800 through a keyboard, a pointing device such as a mouse, or a touch-sensitive surface, such as the display device, via an input device interface 822 or remotely through a web interface, terminal program, or the like via a communication interface 824. The communication interface 824 may be wired or wireless and facilitate communications with any number of devices via a communications network in a direct or indirect fashion. An output device, such as a display device, can be coupled to the system bus 806 and driven by a video port 826. Additional inputs and outputs to the computer system 800 may be provided through the system bus 806 as appropriate to implement embodiments described herein.

The operational steps described in any of the exemplary embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary embodiments may be combined.

Those skilled in the art will recognize improvements and modifications to the preferred embodiments of the present disclosure. All such improvements and modifications are considered within the scope of the concepts disclosed herein and the claims that follow.

What is claimed is:

1. A method for remotely monitoring a physiological parameter, the method comprising:
   sensing optical video data of a subject;
   analyzing the optical video data to track color changes in a region of interest of the subject over a period of time;
   identifying the region of interest on skin of the subject;
   tracking movement of the region of interest across multiple frames of the optical video data; and
   extracting physiological parameter data of the subject by adaptively beamforming the color changes.

2. The method of claim 1, further comprising spatially averaging color changes in the region of interest across the period of time to extract the physiological parameter data.

3. The method of claim 1, wherein changes in more than two colors are tracked over time.

4. The method of claim 3, wherein the color changes are adaptively beamformed using red, green and blue color components.

5. The method of claim 1, wherein extracting the physiological parameter data further comprises spectrally analyzing the color changes after beamforming.

6. The method of claim 1, wherein the physiological parameter is a heart rate of the subject.

7. The method of claim 1, wherein the physiological parameter is a respiration rate of the subject.

8. The method of claim 1, further comprising pre-processing the optical video data to magnify the physiological parameter to be extracted.

9. A device, comprising:
   an optical image sensor; and
   an image processor configured to:
   receive optical video data from the optical image sensor;
   analyze the optical video data to track color changes in a region of interest of a subject over time;
   identify the region of interest on skin of the subject;
   track movement of the region of interest across multiple frames of the optical video data;
   adaptively beamform the color changes;
   analyze the adaptively beamformed color changes to determine a physiological parameter of the subject; and
   extract physiological parameter data of the subject from the analyzed adaptively beamformed color changes.

10. The device of claim 9, wherein the device is an unmanned aerial vehicle (UAV).

11. The device of claim 10, wherein the image processor is further configured to suppress UAV motion artifacts in the optical video data.

12. The device of claim 9, wherein the image processor is further configured to apply a facial recognition algorithm to the optical video data to determine the region of interest on skin of the subject.

13. The device of claim 12, wherein the facial recognition algorithm is further configured to track a corresponding region of interest for each of a plurality of subjects.

14. The device of claim 13, wherein the image processor is further configured to determine the physiological parameter data of each of the plurality of subjects.

15. A vital sign monitoring system, comprising:
   a device comprising an optical image sensor; and
   an image processor in communication with the optical image sensor, the image processor configured to:

receive optical video data from the optical image sensor;
analyze the optical video data to track color changes in a region of interest over time;
identify the region of interest on skin of the subject;
track movement of the region of interest across multiple frames of the optical video data; and
extract physiological parameter data of a human subject by adaptively beamforming the color changes.

16. The vital sign monitoring system of claim 15, further comprising a plurality of unmanned aerial vehicles (UAVs), each of which comprises a corresponding optical image sensor.

17. The vital sign monitoring system of claim 16, wherein the image processor is in communication with each of the corresponding optical image sensors of the plurality of UAVs and further configured to:
analyze optical video data from the corresponding optical image sensor of each of the plurality of UAVs; and
identify corresponding regions of interest for the subject in the corresponding optical video data.

18. A method for remotely monitoring a physiological parameter, the method comprising:
sensing optical video data of a subject;
analyzing the optical video data to track color changes in a region of interest of the subject over a period of time; and
extracting physiological parameter data of the subject by adaptively beamforming the color changes;
wherein the method further comprises at least one of the following features (a) to (c);
  (a) the method further comprises spatially averaging color changes in the region of interest across the period of time to extract the physiological parameter data;
  (b) the method further comprises tracking changes in more than two colors over time; and
  (c) the extracting of the physiological parameter data further comprises spectrally analyzing the color changes after beamforming.

* * * * *